(12) United States Patent
Kulesza

(10) Patent No.: US 7,763,264 B2
(45) Date of Patent: Jul. 27, 2010

(54) COMPOSITION AND METHOD FOR REDUCING THE APPEARANCE OF CELLULITE

(76) Inventor: John Kulesza, 1840 Berlin Turnpike, Wethersfield, CT (US) 06109

( * ) Notice: Subject to any disclaimer, the term of this patent is extended or adjusted under 35 U.S.C. 154(b) by 468 days.

(21) Appl. No.: 11/408,383

(22) Filed: Apr. 21, 2006

(65) Prior Publication Data

US 2006/0258624 A1 Nov. 16, 2006

Related U.S. Application Data

(60) Provisional application No. 60/674,861, filed on Apr. 26, 2005.

(51) Int. Cl.
*A61K 8/02* (2006.01)
(52) U.S. Cl. ..................... 424/401; 424/1.21
(58) Field of Classification Search ................ 424/401, 424/1.21
See application file for complete search history.

(56) References Cited

U.S. PATENT DOCUMENTS

| | | | | |
|---|---|---|---|---|
| 4,761,369 A | * | 8/1988 | Steinman | 435/19 |
| 5,075,113 A | * | 12/1991 | DuBois | 424/450 |
| 5,552,158 A | * | 9/1996 | Evans et al. | 424/450 |
| 5,618,683 A | * | 4/1997 | Brocia et al. | 435/11 |
| 5,716,814 A | * | 2/1998 | Yesair | 435/134 |
| 6,133,463 A | * | 10/2000 | Fourneron et al. | 554/79 |
| 2004/0259948 A1 | | 12/2004 | Tontonoz et al. | |

OTHER PUBLICATIONS

Rotunda, A., Detergent Effects of Sodium Deoxycholate, Dermatologic Surgery, Blackwell Publishing, Jul. 2004, 30:7, p. 1001-1008.*
Schurtenberger, P., Micelle to Vesicle Transition in Aqueous Solutions of Bile Salt and Lecithin, Journal of Physical Chemistry, ACS, 1985, 89, p. 1042-1049.*

* cited by examiner

*Primary Examiner*—Johann R Richter
*Assistant Examiner*—Danielle Sullivan
(74) *Attorney, Agent, or Firm*—Gifford, Krass, Sprinkle, Anderson & Citkowski, P.C.

(57) ABSTRACT

A topical composition for controlling the metabolism and/or distribution of subcutaneous fat and/or moderating the appearance of cellulite, comprising, as an active ingredient, phosphatidylcholine together with a solvent operative to maintain the phosphatidylcholine in solution, and a buffer which maintains the composition in the range of pH 7.5-9.0. Typically, the composition includes less than 10% by weight water. The composition may include further active ingredients such as xanthines. Also disclosed are methods for using the composition.

14 Claims, No Drawings

COMPOSITION AND METHOD FOR REDUCING THE APPEARANCE OF CELLULITE

RELATED APPLICATION

This application claims priority of U.S. Provisional Patent Application Ser. No. 60/674,861 filed Apr. 26, 2005, entitled "Composition and Method for Reducing the Appearance of Cellulite."

FIELD OF THE INVENTION

This invention relates generally to methods and materials for treating lipidostrophies such as cellulite. More specifically, the invention relates to a therapeutic material and method which controls the metabolism and/or distribution of subcutaneous fat and operates to control the appearance of cellulite. Specifically, the invention relates to compositions and methods based upon the use of phosphatidylcholine as an active ingredient.

BACKGROUND OF THE INVENTION

Lipidostrophic conditions involve the abnormal distribution of fat in tissues such as: under the eyes, chin, hips, and thighs. Cellulite is one lipidostrophy wherein subcutaneous fat deposits cause the skin to have a coarse texture variously described as "orange peel" or "cottage cheese." The condition is believed to be attributable to a combination of fat storage and distribution and edema in the connective tissue resultant from mild lymphatic blockage with some connective tissue involvement. The condition occurs most frequently in women.

Various therapies have been proposed for the treatment of cellulite ranging from surgery to injections of therapeutic material. However, since cellulite is generally not considered to be a condition posing a serious threat to general health, such invasive treatments are not generally justified. In some instances, transdermal applications of anti-estrogens or androgenic materials have been employed to alter the physiology of subcutaneous tissue in an attempt to reverse the appearance of cellulite. In other instances, therapeutic materials such as transition metal compositions have been used in an attempt to bind collagen and elastic fibers so as to thicken the skin and thereby eliminate the appearance of cellulite. Such therapies are shown for example in U.S. Pat. Nos. 6,071,526 and 6,358,539. In other instances, compositions including theophylline and other such xanthine compounds have been employed to control cellulite. Therapies of the prior art have limited efficacy and/or undesirable side effects; therefore, there is still a need in the prior art for a safe and effective method for treating cellulite and other such lipidostrophies.

As will be explained in greater detail hereinbelow, the present invention is directed to a composition which employs phosphatidylcholine as an active ingredient for controlling the metabolism and/or distribution of subcutaneous fat. While phosphatidylcholine has been used topically in a number of compositions for the treatment of the skin, it has not previously been shown to be effective as an agent which penetrates the dermal barrier and actively influences fat metabolism and/or distribution. In fact, in the prior art, phosphatidylcholine has primarily been used as an ingredient for forming liposomes and like micellar structures used to encapsulate active ingredients. In general, the prior art has recognized and taught that phosphatidylcholine itself is incapable of penetrating the dermal barrier in the absence of penetration-facilitating agents such as surfactants and the like used in a micellar structure. In this regard see U.S. Published Patent Application 2003/0039668.

The present invention is directed to a topical preparation which is active to control fat distribution and metabolism. These compositions can be used to treat various lipidostrophies, and will be discussed primarily with reference to their use in reducing the appearance of cellulite. However, it is to be understood that the compositions have utility in treating other conditions involving fat distribution.

BRIEF DESCRIPTION OF THE INVENTION

Disclosed herein is a topical composition for controlling the metabolism and/or distribution of fat and/or the appearance of cellulite. The compositions of the present invention include phosphatidyl choline, together with a solvent which is operable to maintain the phosphatidyl choline in solution, and a buffer which is operable to maintain the pH of the composition in the range of 7.5-9.0. In specific instances, the phosphatidyl choline comprises, on a weight basis, 5-50% of the composition. Solvents used in the present invention may comprise water-miscible solvents such as alcohols, ethers, glycols, glycol ethers and esters, used either singly or in combination.

The composition of the present invention may further include a secondary active ingredient such as xanthine, and some such xanthines include caffeine, theophylline, theoxanthine, theobromine, and aminophylline, and these materials may be used either singly or in combination. The composition may include ancillary ingredients such as thickeners, surfactants, fragrances, coloring agents, chelating agents and the like.

Also disclosed are methods for altering the metabolism and/or distribution of fat and/or reducing the appearance of cellulite. The methods involve the topical application of the formulations of the present invention to a portion of the body. The compositions may be applied on an at least daily basis, and application of the material may be followed by the application of a lipid barrier restorative agent to the skin.

DETAILED DESCRIPTION OF THE INVENTION

The present invention comprises a composition, suitable for topical application, which readily penetrates dermal layers and exerts a therapeutic effect on underlying tissues so as to reduce or eliminate the appearance of cellulite. The composition includes a preparation of biologically active phosphatidylcholine which is dissolved in an appropriate solvent so as to be in molecular form. While not wishing to be bound by speculation, Applicant believes that the solubilized phosphatidylcholine penetrates the skin and accumulates in fatty tissues where it triggers a release of lipase enzymes which break down lipids which are a factor in cellulite. It is also believed that the phosphatidylcholine emulsifies cell membranes and intercellular fats thereby further decreasing the appearance of cellulite.

The composition further includes a buffering agent which maintains the composition at a pH in the range of 7.5-9.0, and preferably approximately 8.0, and thereby inhibits the breakdown of the phosphatidylcholine into its constituent diacyl glycerol and phosphatidic acid in the skin by the phospholipase C enzyme. In addition to, or instead of the buffer, compositions of the present invention may include other agents for inhibiting the phospholipase C enzyme. There are a variety of buffering agents which may be employed in the practice of the present invention, and one of skill in the art can select an appropriate buffer to maintain the desired slightly alkaline pH range of 7.5-9.0. One buffer which may be employed in the present invention comprises a mixture of tromethamine and its hydrochloride salt. Buffers of this type are commercially available under the product name Trizma 8.0. Other buffers such as citric acid/sodium citrate and phosphoric acid/sodium phosphate systems may be likewise employed.

In the compositions of the present invention, the phosphatidylcholine is solubilized, and is in a molecular form. For this reason, and in contrast to generally accepted wisdom in the prior art, the phosphatidylcholine readily penetrates the skin and interacts with underlying tissues. This is in contrast to various prior art therapeutic compositions wherein phosphatidylcholine is disposed in multiphase structures such as oil-containing vesicles, lamellae, liposomes or other such structures ("micellar structures") which prevent its activity.

The solvent component of the composition of the present invention should be capable of fully solubilizing the phosphatidylcholine and other ingredients of the composition. Organic solvents comprise one preferred group of solvents. There are a wide variety of organic solvents which may be utilized in the practice of the present invention. Since phosphatidylcholine can form micellar structures in the presence of significant amounts of water, compositions of the present invention generally have a low content of water. Typically, compositions having physiologically active levels of phosphatidylcholine will contain no more than 10% water. Such compositions will have the phosphatidylcholine in solution and will not manifest a micellar structure. Any solvent should be compatible with the topical application of the formulation to the skin. Such solvents may include alcohols, ethers, esters, polyols such as glycols, glycerols, and the like as well as glycol ethers, lipids and various combinations thereof. One solvent system which has been utilized in the practice of the present invention comprises a mixture of ethyl alcohol and diethylene glycol ethyl ether. Other such solvent systems will be readily apparent to those of skill in the art.

In specific embodiments, further ingredients may be added to the composition. Such ingredients may include a surfactant material which aids in the wetting of the skin with the composition and thereby enhances penetration. One group of surfactants comprises cationic surfactants, and one particular surfactant which may be utilized in the present invention comprises hexadecyltrimethylammonium bromide (CTAB). This material is a cationic surfactant, and also functions as an antiseptic and/or esterase inhibitor.

Compositions of the present invention may further include stabilizing and preservative agents. For example, the compositions may include a chelating agent such as EDTA and/or its salts. EDTA may also function to inhibit esterase activity. Preservatives, and in specific instances antioxidants such as BHT, may be included to stabilize the composition.

The composition of the present invention may also include further active ingredients having therapeutic utility. For example, the composition may include a xanthine; and one particular group of xanthines is methylated purine alkaloids such as caffeine, theobromine, theoxanthine, theophylline, and other variants thereof including synthetic variants such as aminophylline. Other xanthines having utility comprise ephedrine as well as its variants and derivatives. In one particular embodiment of the present invention, the composition further includes a mixture of caffeine and aminophylline-related botanicals, and one such mixture is commercially available under the brand name Lipocare from the Sederma Corporation. This material comprises a mixture of caffeine, butylene glycol, PEG-8, Bupleurum falcatum (extract) and coenzyme A. Coenzyme A is a mediator of fatty acid transport in mitochondria, and topical application may enhance the clearance of fatty acids created by the breakdown of adipocytes by phosphatidylcholine.

The compositions of the present invention may further include coloring agents, fragrances, and the like as well as gelling or thickening agents. In one specific embodiment, the composition includes a hydroxyl propyl cellulose thickener material such as the material sold under the brand name Klucel.

Within the foregoing parameters, various compositions may be prepared in accord with the present invention. In this application, all percentages, unless otherwise stated, will be on the basis of weight. In general, the phosphatidylcholine will be present in the compositions in the range of 5-50%, and in one particular group of compositions it comprises approximately 12% thereof. The buffer material is generally present in a relatively small amount as is sufficient to maintain the proper pH range. In those instances where the buffer comprises the aforementioned tromethamine-based material, it is typically present in an amount of approximately 0.1-1% of the composition, and in a specific embodiment comprises 0.6% of the composition. Surfactant materials are likewise generally present in a similar range of percentages and the foregoing CTAB surfactant comprises, in a particular embodiment, 0.8% of the composition. Preservatives and stabilizers are generally present in relatively low amounts, typically in the range of 0.1-1%. For example, when tetrasodium EDTA is present in a specific embodiment it comprises 0.06% of the composition, and when BHT is utilized it comprises 0.03% of the composition.

In those instances where auxiliary ingredients such as the aforementioned xanthines are employed, they typically comprise 0.1-10% of the composition. As mentioned previously, a commercial product sold under the brand name Lipocare, and comprising a caffeine/botanical mixture, may be utilized as an auxiliary active ingredient, and in such instances, this material comprises 3.0% of the composition.

Thickening agents such as the aforementioned hydroxy propyl cellulose are typically employed in relative low percentages, and to the extent necessary to provide a desired degree of viscosity to the composition. Typically such materials comprise 1-5% of the composition, and in a specific embodiment, the aforementioned hydroxyl propyl cellulose comprises 2.2% of the composition.

The solvent component generally comprises the remainder of the composition, and typically is present in a range of 30-70% of the composition. In a specific embodiment, the solvent comprises a mixture of 43.31% of diethylene glycol ethyl ether, 30% of denatured ethyl alcohol and approximately 5% water.

The compositions of the present invention may be readily prepared by blending together the aforementioned ingredients. In one specific preparation, water, tetrasodium EDTA, and the Trizma 8.0 buffer are, in a first step, mixed to form a clear solution. In a second step, the diethylene glycol ethyl ether, alcohol, BHT, and the CTAB surfactant are separately mixed to form a clear solution. In a third step, the solution prepared in the first step and the solution prepared in the second step are mixed together and stirred until a clear final solution is obtained. In a fourth step, phosphatidylcholine and the Lipocare product (if utilized) are added to this solution and mixed until a clear final solution is obtained. Thereafter, the hydroxyl propyl cellulose thickener is stirred into the mixture with a vortex stirrer and mixing continued until a clear gel forms.

The compositions of the present invention are effective when applied to the skin in a topical manner. Typically, the composition is applied one to two times daily. In some instances, application of the material of the present invention is followed with treatment with a lipid replenishing moisturizer material, which may or may not include an antihistamine. The function of the secondary application of the moisturizing material is to restore any lost moisture barrier function to the skin which may be caused by use of the present therapeutic composition. Other modes of application, including sustained release applicators such as bandages, gels, and other topical delivery devices, may be employed, for example, for overnight applications. In some instances, various penetration-enhancing devices and procedures may be used to increase the efficacy of the invention. These can include chemical peels, microdermabrasion, heat, light treatments such as LED and laser light, as well as other techniques such as ultrasound and iontophoresis.

In view of the teaching presented herein, yet other compositions and modes of use will be readily apparent to those of skill in the art. The foregoing discussion and description is illustrative of specific embodiments, but is not meant to be a limitation upon the practice of the present invention. It is the following claims, including all equivalents, which define the invention.

The invention claimed is:

1. A topical composition for controlling the metabolism and/or distribution of fat and/or the appearance of cellulite, said composition comprising:
    phosphatidylcholine;
    a buffer operative to maintain the pH of the composition in the range of 7.5-9; and
    a solvent operative, and in a sufficient amount to maintain all of said phosphatidylcholine in solution so that said composition exhibits no micellar structure.

2. The composition of claim 1, wherein said phosphatidylcholine comprises, on a weight basis, 5-50% of said composition.

3. The composition of claim 2, wherein said phosphatidylcholine comprises 12 weight percent of said composition.

4. The composition of claim 1, wherein said buffer is operative to maintain said composition at a pH of 8.

5. The composition of claim 1, wherein said solvent includes a member selected from the group consisting of alcohols, ethers, esters, glycols, glycol ethers, and combinations thereof.

6. The composition of claim 1, further including a xanthine selected from the group consisting of caffeine, theophylline, theoxanthine, theobromine, aminophylline, and combinations thereof.

7. The composition of claim 1, further including a surfactant.

8. The composition of claim 1, further including a chelating agent.

9. A method for altering the metabolism and/or distribution of fat, and/or reducing the appearance of cellulite in a body, said method comprising: topically applying to a portion of said body a non-micellar composition comprising phosphatidylcholine, a solvent operable to maintain all of said phosphatidylcholine in solution, and a buffer operative to maintain the solution at a pH in the range of 7.5-9.0.

10. The method of claim 9 wherein said step of applying the composition comprises applying the composition on an at least daily basis.

11. The method of claim 9 comprising the further step of applying a lipid barrier restorative agent to said skin after the step of applying said composition thereto.

12. The method of claim 11, wherein said restorative agent further includes an antihistamine.

13. A topical composition for controlling the metabolism and/or distribution of subcutaneous fat and/or the appearance of cellulite, said composition comprising:
    a first active ingredient consisting essentially of phosphatidylcholine;
    optionally, a second active ingredient consisting essentially of a member selected from the group consisting of: a xanthine, coenzyme A, Bupleurum falcatum extract, and combinations thereof;
    a solvent which dissolves all of said active ingredients and maintains them in solution so that said composition has no micellar structure;
    a buffer which maintains the pH of said composition in the range of 7.5-9.0; and
    optionally, an ancillary ingredient selected from the group consisting of: thickeners, surfactants, coloring agents, chelating agents, fragrances, and combinations thereof.

14. The composition of claim 13, further characterized in that it includes no more than 10% by weight of water.

* * * * *